United States Patent [19]
Stevens

[11] Patent Number: 5,599,319
[45] Date of Patent: Feb. 4, 1997

[54] SOFT FLEXIBLE CATHETER TIP FOR USE IN ANGIOGRAPHY

[75] Inventor: Robert C. Stevens, Williston, Fla.

[73] Assignee: Cordis Corporation, Miami Lakes, Fla.

[21] Appl. No.: 520,576

[22] Filed: Aug. 29, 1995

Related U.S. Application Data

[63] Continuation-in-part of Ser. No. 299,841, Sep. 1, 1994, Pat. No. 5,514,108.

[51] Int. Cl.[6] .................................................. A61M 5/00
[52] U.S. Cl. ........................... 604/264; 604/283; 604/280
[58] Field of Search .................................. 604/280–282, 604/264, 138, 172–173, 154, 121; 138/121, 173

[56] References Cited

U.S. PATENT DOCUMENTS

| | | |
|---|---|---|
| D. 263,873 | 4/1982 | Genese . |
| 1,477,695 | 4/1920 | Dolge et al. . |
| 3,485,234 | 4/1966 | Stevens . |
| 4,576,772 | 3/1986 | Carpenter . |
| 4,596,563 | 6/1986 | Pande . |
| 4,661,094 | 4/1987 | Simpson . |
| 4,731,054 | 3/1988 | Billeter et al. . |
| 4,838,879 | 6/1989 | Tanabe et al. . |
| 5,017,259 | 5/1991 | Kohsai . |
| 5,088,991 | 2/1992 | Weldon . |
| 5,358,493 | 10/1994 | Schweich, Jr. et al. . |

*Primary Examiner*—Corrine M. McDermott
*Assistant Examiner*—Perry E. Van Over
*Attorney, Agent, or Firm*— Fay, Sharpe, Beall, Fagan, Minnich & McKee

[57] ABSTRACT

A plurality of regions of a first transverse rigidity are formed in the flexible tip portion of a catheter having a second transverse rigidity along its length which is greater than the first transverse rigidity. The regions of the lesser first transverse rigidity are formed by areas of the catheter tip having an average transverse cross-sectional area less than a transverse cross-sectional area of the remainder of the catheter apparatus. The plurality of first transverse rigidity regions are formed by a respective plurality of circumferential cut-out regions in the catheter tip.

6 Claims, 2 Drawing Sheets

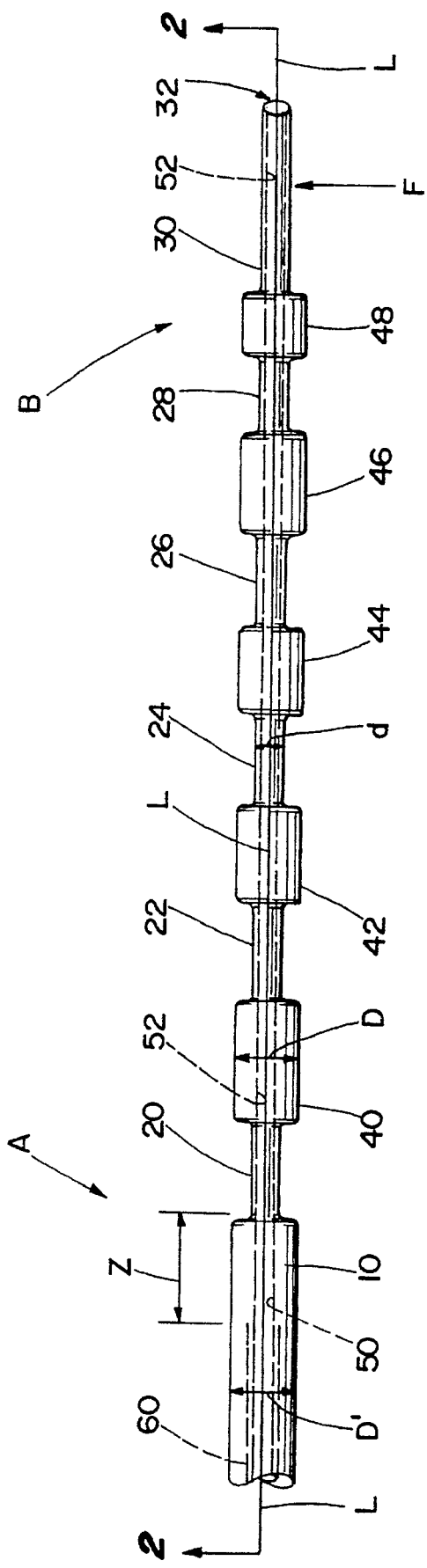
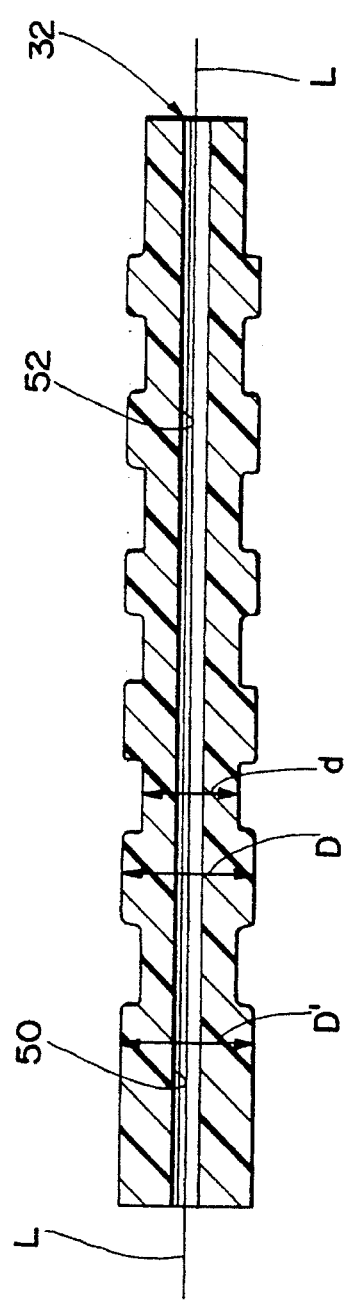
Fig. 1
Fig. 2

5,599,319

SOFT FLEXIBLE CATHETER TIP FOR USE IN ANGIOGRAPHY

This application is a continuation-in-part of U.S. application Ser. No. 08/299,841, filed Sep. 1, 1994 now U.S. Pat. No. 5,514,108 for "Soft Flexible Catheter Tip For Use In Angiography."

BACKGROUND OF THE INVENTION

The instant invention relates to a catheter apparatus having a soft flexible tip adapted for use with a steel guide wire in procedures including angiography and will be described with particular reference thereto. However, it is to be appreciated that the invention finds application in other procedures where catheters are inserted generally into the human body cavity.

In the practice of catheterization and in particular angiography, a hollow catheter is inserted by well known means into the vascular system of a patient, usually through the femoral artery, and advanced toward a target site where an opaque media is delivered under pressure. During the procedure, it is important to accurately route the catheter through the appropriate branching vessels within the body. For this purpose, a small bend is oftentimes placed on or formed by the catheter tip so that rotational motion about the longitudinal axis of the catheter while advancing same effects a "steering" of the tip through the system.

In order to prevent damage to the patient yet provide a workable apparatus, the catheter tip must be both soft so as to be incapable of distending or piercing the surrounding vessels yet transversely rigid enough to withstand both the motion of blood flow as well as stand-up under the opaque media delivery pressure.

A catheter tip that is too soft tends to curl upon itself and become lodged in the tissue and vessel wall. Further, a tip which is too soft to be forced into and through the vessel at the artery site, such as into the femoral artery, is of little utility at all. Catheter tips which are too rigid are difficult to control as they are routed to the target site. Damage to the vessels and arteries or other body tissue may result from the use of stiff catheter tips.

SUMMARY OF THE INVENTION

The present invention contemplates a new and improved flexible catheter tip apparatus adapted to be guided through blood vessels. The catheter tip of the invention includes at least one region of a transverse rigidity disposed in the flexible catheter tip being different from the average overall transverse rigidity of the remainder of the catheter device. The catheter apparatus includes an elongate tubular member having a substantially uniform first transverse rigidity while the flexible tip portion of the catheter device includes a series of portions of varying transverse rigidity to provide a region of a second average transverse rigidity less than the first transverse rigidity.

According to another aspect of the invention, the second average transverse rigidity of the at least one region of the flexible catheter tip varies along the longitudinal axis of the flexible tip portion.

According to a further aspect of the invention, the at least one region of varying second transverse rigidity is defined by a portion of the flexible tip having an average transverse first cross-sectional area along the longitudinal axis of the catheter which is less than a transverse second cross-sectional area of the remainder of the catheter flexible tip.

According to still another aspect of the invention, at least one region of varying second average transverse rigidity includes a plurality of portions, each of the plurality of regions having a respective transverse rigidity less than the first transverse rigidity. More particularly, the regions of lesser transverse rigidity can be provided by areas of lesser wall thickness as, for example, results from a construction which is in the nature of a series of rings of differing outer diameter but of common inner diameter.

According to yet another aspect of the invention, the catheter includes a single, uniform longitudinal bore formed therethrough which serves as a conduit for the transport of opaque media during surgical procedures.

An advantage of the invention is that it provides an improved surgical risk quotient whereby the chances of injury to the patient are minimized.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein:

FIG. 1 is a side view of the distal end region of an angiographic catheter in accordance with the present invention;

FIG. 2 is a longitudinal cross-sectional view of the angiographic catheter of FIG. 1 taken along line 2—2;

DETAILED DESCRIPTION OF THE PREFERRED EMBODIMENTS

Figure 3:
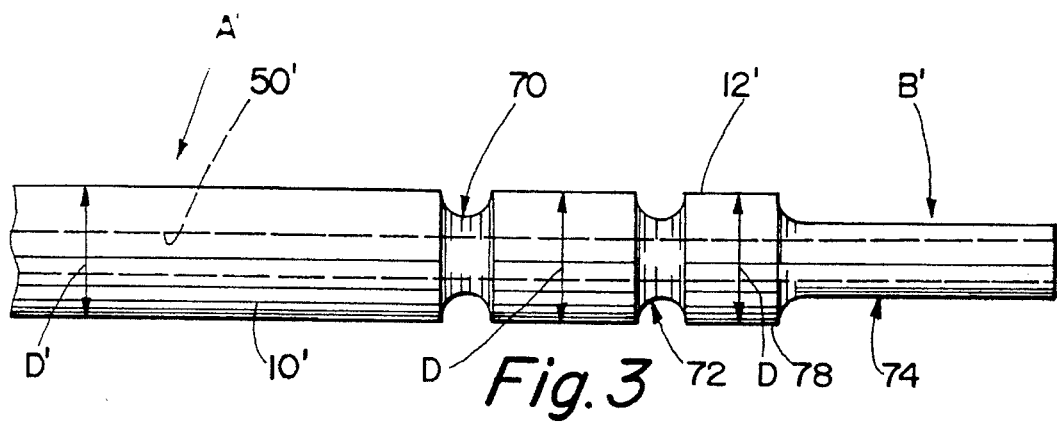
FIG. 3 is a side view of the distal end region of an angiographic catheter formed in accordance with a second embodiment of the present invention.

Referring now to the drawings wherein the showings are for the purpose of illustrating preferred and alternate embodiments of the invention only and not for purpose of limiting same, the FIGS. 1 and 2 show (not to scale) a catheter device A having a distal end B adapted to be guided through blood vessels of a human patient. More particularly, and with reference first to FIG. 1, the catheter device A forms an elongate tubular body member 10 which connects the proximal end (not shown) of the catheter device with the distal end B for conducting opaque media from an operatively associated source of the media to the distal end B. A flexible tip portion 12 is formed at the distal end B of the catheter device A.

According to the preferred embodiment the flexible tip portion includes a plurality of regions having a transverse rigidity different than the transverse rigidity inherent in the construction of the elongate tubular body member 10. For the purposes of this detailed description, "transverse rigidity" defines that property of an elongate body which tends to resist bending in a direction substantially perpendicular to the longitudinal axis of that elongate body. With reference to FIG. 1, the transverse rigidity of the catheter device shown there is its ability to resist bending due to forces such as shown at F which are generally applied perpendicular and generally transverse to the longitudinal axis L of the catheter. The transverse rigidity of the present invention varies from the distal end longitudinally to the proximal end and the average transverse rigidity of the tip portion 12 decreases from body 10 to the distal end and is less than the transverse rigidity of body 10.

With continued reference to FIG. 1, in the preferred embodiment, the varying regions of transverse rigidity formed in the flexible tip portion 12 are generated by a plurality of cut-out regions 20–30 which may either be formed in the flexible tip portion during its manufacture or defined thereon in one or more additional manufacturing step(s) such as a cutting or roll forming operation.

The plurality of cut-out regions 20–30 define a plurality of spaced circumferential rings 40–48 arranged on the flexible tip portion 12. Each of the plurality of circumferential rings 40–48 preferably having the same outer diameter D as the outer diameter D' of the elongate tubular body member 10.

With respect to specific dimensional relationships, it is clear that these could vary substantially. In addition, the dimensions could, and normally should, vary between different catheter tip sizes. For example, there are currently standard catheter sizes referred to as "French" sizes, e.g., size F4 is 0.053 inch diameter, F5 is 0.066 inch diameter, F6 is 0.079 inch diameter, F7, is 0.092 inch, and F8, is 0.104 inch. It is believed that the subject invention is applicable to all these sizes. To provide a full and complete enabling disclosure, a preferred set of specific dimensions for the most commonly used F7 size is as hereafter set forth. Suitable dimensions for the remaining sizes can be readily determined by simple extrapolation and minor experimentation.

According to the embodiment of FIGS. 1 and 2, and with respect to a size F7 catheter, the outer diameter of the circumferential rings D as well as the outer diameter D' of the elongate tubular body member 10 is 0.092 inch. Further, each of the plurality of cut-out regions 20–30 generate a reduced diameter d at spaced positions along the flexible tip portion 12. The diameter of regions 20–30 progressively decrease with region 20 being 5% less than D; region 22 being 10% less, region 24 being 15% less, region 26 being 17% less, region 28 being 20% less and region 30 being 25% less.

Further, in this embodiment, each of the first through fifth cut-out regions 20, 22, 24, 26, and 28 are of decreasing width along the longitudinal axis L of, respectively, 0.312 inches, 0.250 inches, 0.218 inches, 0.187 inches, and 0.156 inches. The sixth cut-out region 30 extends from the fifth circumferential ring 48 to the opening 32 at the distal end B of the catheter device and is approximately 0.500 inches in length.

With continued reference to FIG. 1, pairs of the cut-out regions 20–30 define the circumferential rings 40–48. The first circumferential ring 40 is the widest and has a width along the longitudinal axis L of the same width as the preceding cut-out region 20. The second through fourth circumferential rings 42, 44 and 46, in turn, have widths which are equal to the width of the immediately preceding circumferential section. That is, circumferential ring 48. The second through fourth circumferential rings 42–46 have a width along the longitudinal axis L of 42 is 0.250 inches, 44 is 0.218 inches, 46 is 0.187 inches, while the width of the fifth circumferential ring 48 is 0.156 inches.

A preferred material is a flexible polyurethane which is available from G. F. Goodrich under the trade name Estane 58091/58092. This material is preferred because of its excellent torque response, i.e., resistance to torsional twisting about the longitudinal axis L, and its ability to withstand high pressures such as when an opaque media is injected into an artery or other blood vessel. The tip material is Estane 58092 only. This gives the desired flexibility. The combination of this preferred polyurethane material with the tip construction described above, provides excellent tip guide response.

Also with reference to FIG. 2, the lumen 50 of the elongate tubular body member 10 is illustrated as being co-extensive with approximately the same dimensions as the lumen 52 of the flexible tip portion 12. In the F7 size of the preferred embodiment, the diameter of the lumens of the elongate tubular body member 10 as well as the flexible tip portion 12 is between 0.046 and 0.056 inches.

Figure 4:
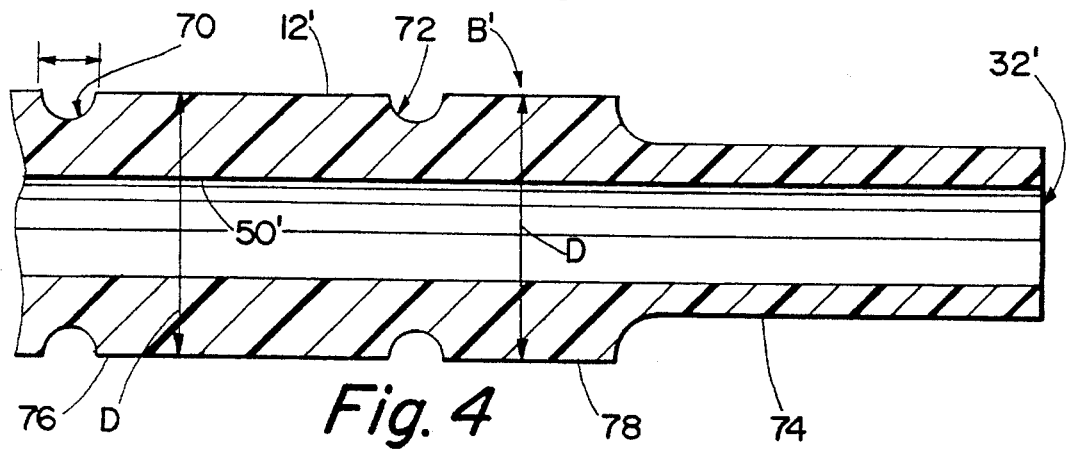
FIG. 4 is a longitudinal cross-sectional view of the FIG. 3 embodiment.

FIGS. 3 and 4 show a second embodiment of the invention which achieves the desired varying regions of transverse rigidity by using a modified shape for the cutouts. In the description of this second embodiment, the same reference numerals differentiated by a prime suffix (') have been used to identify the elements which correspond to those by the FIGS. 1 and 2 embodiment. The description given for such an element in the FIGS. 1 and 2 embodiment is to be taken as equally applicable to the FIGS. 3 and 4 embodiment unless otherwise noted.

With particular reference to FIG. 3, the varying regions of transverse rigidity in the flexible tip portion 12' are generated by a plurality of cut-out portions 70, 72, and 74 which are formed in the manufacture of the tip by being molded, rolled, or cut therein. The cut-out regions 70, 72, and 74 define a pair of spaced, circumferential rings 76, 78; however, it is recognized that a greater number of cut-out regions could be provided.

As in the FIGS. 1 and 3 embodiment, the rings 76, 78 have a diameter D that is equal to outer diameter D' of the tubular body member 10'.

Figure 6:
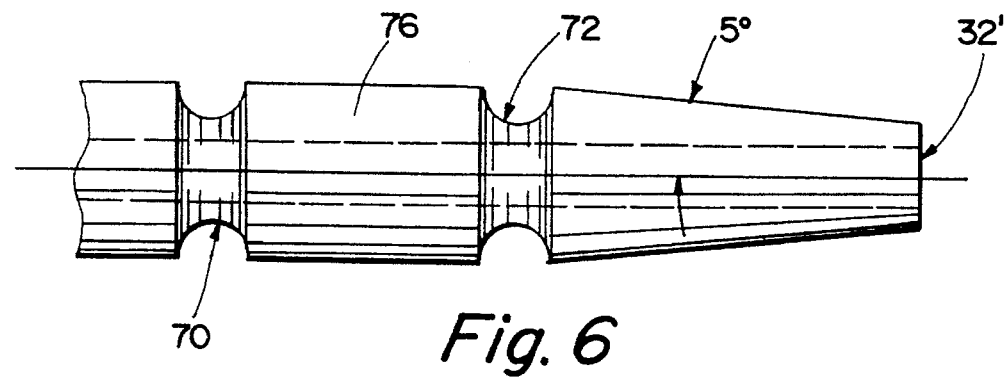

With reference to the cut-out regions 70, 72, it will be noted that these are rounded at the base to have less tendency to kink. A semi-circular cross section is preferred although other rounded forms such as semi-elliptical or the like could be used. The final or end cut-out 74 is about 0.50 inches long and has a rounded corner. The cut-out 74 extends to the end opening 32 with a constant diameter. It is possible to terminate the tip in a gradually tapered end such as shown in FIG. 6. A tip of this nature can be used for a variety of purposes and the taper could vary but is shown as a 5° taper relative to the longitudinal center axis.

It should also be noted that it is believed that the narrower cut-outs in the FIGS. 3 and 4 embodiment as compared to the FIGS. 1 and 2 embodiment yields more desirable characteristics. For example, when applied to a F7 size catheter, a width for the cut-outs of about 0.060 inches is preferred. The same width can be used on other size catheters. A depth of cut-out of approximately 0.015 has been found suitable for a F7 size catheter. In other catheter sizes, however, a depth of in the range of approximately 16% of the catheter diameter has been found suitable.

As regards the width of the circumferential rings, these can also vary but, preferably, they are in the range of 0.100 to 0.150 inches for all sizes of catheters.

The FIGS. 3 and 4 embodiment can be formed from the same material as the FIGS. 1 and 2 embodiment. In its preferred form, however, a slightly softer and more flexible Estane 58271 shore 80A is used.

Figure 5:
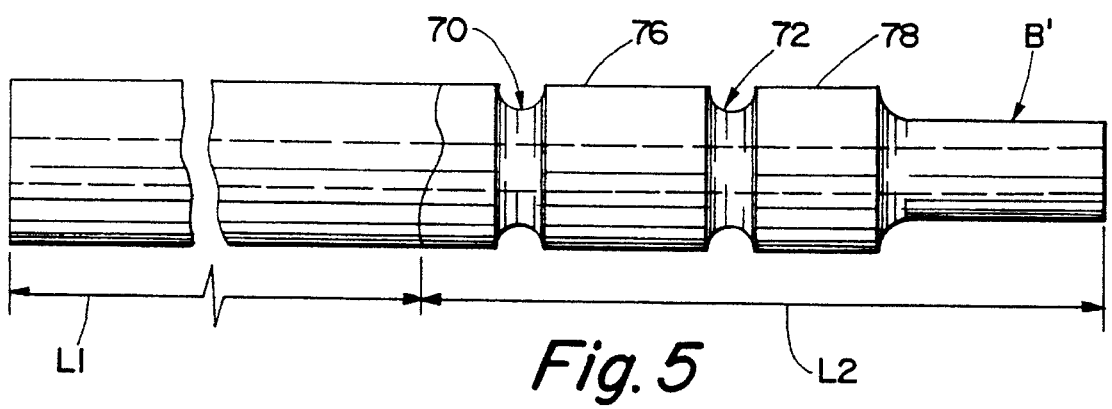
FIG. 5 is a side view of the distal end region of an angiographic catheter formed in accordance with a third embodiment of the present invention; and, FIG. 6 is a side view of an alternative end form for the embodiment of FIGS. 3 and 4.

An alternative form of the FIGS. 3 and 4 embodiment is shown in FIG. 5. In this form, Estane 58092 is used in the proximal 2¼" (L1) portion of a 3" tip and Estane 58271 shore 80A is used in the distal ¾" (L2) portion. These two pieces are fused or molded together.

Although the soft flexible catheter tips described above in connection with the preferred embodiments include a plurality of circumferential rings defined by a corresponding plurality of cut-out regions, alternative embodiments are also contemplated such as spiral cut-out or built-up regions or combinations of circumferential ring and/or spiral regions. Partially circumferentially extending regions are also possible alone or in combination with the above alternatives.

In addition, the present invention contemplates any and all patterns which may be formed on or in the flexible tip portion which define at least one region in the flexible tip portion of a transverse rigidity which is different than that defined by the elongate tubular member and the remainder of the catheter.

The invention has been described with reference to preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, I now claim:

1. A catheter having a distal end adapted to be guided through blood vessels, comprising:

an elongate tubular member formed of a first polyurethane material and having i) a first innerbore of uniform diameter therethrough along a longitudinal axis of the elongated tubular member and ii) a substantially uniform first transverse rigidity;

a flexible tip portion formed of a second polyurethane material bonded at a distal end of said elongated tubular member and having a second innerbore of uniform diameter therethrough along a second longitudinal axis of the flexible tip portion which is generally coextensive with said first longitudinal axis of the elongated tubular member, said second polyurethane material being softer and more flexible than said first polyurethane material; and, at least one region of a lesser second transverse rigidity on said flexible tip portion formed by at least two areas of decreasing transverse rigidity, said areas of decreasing transverse rigidity provided by circumferentially extending cut-out portions extending radially into the tip and terminating in a rounded bottom wall, said cut-out portions having a width of 0.100 to 0.150 inches.

2. The catheter according to claim 1 wherein said at least one region of lesser rigidity is provided by a series of uniform diameter sections located between the cut-out portions.

3. The catheter apparatus according to claim 2 wherein said tubular tip portion includes a pliable leading tip zone defining the distal end of the catheter apparatus.

4. The catheter apparatus according to claim 3 wherein said leading tip zone is frustoconical and formed from a soft polyurethane material different from the polyurethane material forming said tubular body portion.

5. The catheter apparatus according to claim 3 wherein said frustoconical leading tip zone has a taper angle of approximately 5°.

6. The catheter apparatus according to claim 2 wherein the second polyurethane material is Estane 58092.

\* \* \* \* \*